(12) United States Patent
Kuwayama et al.

(10) Patent No.: US 8,524,128 B2
(45) Date of Patent: Sep. 3, 2013

(54) METHOD FOR PRODUCTION OF POROUS CERAMIC MATERIAL

(75) Inventors: Tomoya Kuwayama, Kurashiki (JP); Yuji Hotta, Kurashiki (JP)

(73) Assignee: Kuraray Co., Ltd., Kurashiki-shi (JP)

( * ) Notice: Subject to any disclaimer, the term of this patent is extended or adjusted under 35 U.S.C. 154(b) by 0 days.

(21) Appl. No.: 12/531,127

(22) PCT Filed: Mar. 4, 2008

(86) PCT No.: PCT/JP2008/053864
§ 371 (c)(1), (2), (4) Date: Sep. 14, 2009

(87) PCT Pub. No.: WO2008/111432
PCT Pub. Date: Sep. 18, 2008

(65) Prior Publication Data
US 2010/0112330 A1  May 6, 2010

(30) Foreign Application Priority Data
Mar. 12, 2007  (JP) .................. 2007-062282

(51) Int. Cl.
*B28B 1/00* (2006.01)
(52) U.S. Cl.
USPC ........................................ 264/28

(58) Field of Classification Search
USPC ........................................ 264/28
See application file for complete search history.

(56) References Cited

FOREIGN PATENT DOCUMENTS

| JP | 63-021219 A | 1/1988 |
|---|---|---|
| JP | 2004-275202 A | 10/2004 |
| JP | 2004-307294 A | 11/2004 |
| JP | 2005-001943 A | 1/2005 |

OTHER PUBLICATIONS

Machine Translation of JP 2004-275202.*
Machine Translation of JP 2004-307294.*
Kokubo Et Al. "Formation of Zirconia Fibers on Unidirectional Freezing of a Gel", J. of Mat. Sci. 23 (1988) pp. 1126-1130.*

* cited by examiner

*Primary Examiner* — Joseph S Del Sole
*Assistant Examiner* — Russell Kemmerle, III
(74) *Attorney, Agent, or Firm* — Leydig, Voit & Mayer, Ltd.

(57) ABSTRACT

The invention provides a method of producing a porous ceramics material. The method comprises preparing a slurry by dispersing a ceramics raw material in a medium, filling the slurry in a container, inserting the container in a given direction into a cooling medium having a temperature not higher than the freezing point of the slurry such that the slurry freezes unidirectionally from one end side, drying the frozen slurry to give a green body, and firing the green body.

5 Claims, 10 Drawing Sheets

11 porous ceramics material
21 slurry
31 container
41 cooling medium 11 porous ceramics material
21 slurry
31 container
41 cooling medium (A)

(B)

(A)

(B)

(C)

(A)

(B)

METHOD FOR PRODUCTION OF POROUS CERAMIC MATERIAL

TECHNICAL FIELD

The present invention relates to a production method of a porous ceramics material.

BACKGROUND ART

Among the ceramics materials, calcium phosphate-based ceramics material is a main component of bone and tooth, has superior biocompatibility, and is superior in the safety. Therefore, it is widely utilized and studied as a biomaterial such as a medical or dental implant material to be implanted in the living body such as artificial bone, artificial dental root and the like, scaffold for cell culture to be used for regenerative medicine and the like, a drug carrier for drug delivery system (DDS) and the like.

Among these, the research and development are particularly actively performed in recent years of ceramics materials suitable for an artificial bone used for repairing or healing by filling in a defect or hole made in the bone due to a disease such as bone fracture, bone tumor and the like or a treatment thereof. Although ceramics materials are already used widely in the clinical practice, current ceramics materials are defective in that the new bone formation after implantation into an affected part is limited to the surface layer of the material and the strength is not sufficient, thereby prolonging the time necessary for healing the injury.

Accordingly, the development of a ceramics implant material, scaffold for cell culture and the like, which allow a biological tissue to rapidly penetrate into the inside and quickly form a tissue (new bone), and has a practical strength, is desired.

As such ceramics implant material, (1) calcium phosphate-based sintered body wherein many pores are densely distributed three-dimensionally, and a skeleton wall compartmentalizing adjacent pores has linked sphere-like opened pores communicating with them (see patent document 1), (2) a method of forming bead-shaped porous ceramics materials having pores by connecting them with a nylon wire and the like (see patent document 2) and the like are suggested.

Moreover, it is disclosed that a sintered body having unidirectionally-oriented penetrating pores with a diameter of 10-500 µm is a ceramics material suitable as an implant material (see patent documents 3, 4).

On the other hand, a method of obtaining various structures such as honeycomb-shaped structure, fiber-like structure and the like is known, which comprises descending and immersing a sol comprising water or a subliming substance such as tert-butyl alcohol and the like as a medium into a cooling medium, thus allowing the crystal of the medium to unidirectionally freeze, obtaining a frozen body by the use of the crystal as a template, and removing the medium (see patent document 5 and non-patent documents 1-3).
patent document 1: JP-B-3470759
patent document 2: JP-A-2003-335574
patent document 3: JP-A-2004-275202
patent document 4: JP-A-2005-1943
patent document 5: JP-A-2004-307294
non-patent document 1: The Yogyo Kyokai shi (Journal of the Ceramics Association, Japan) vol. 93 (7), 1985, p. 387
non-patent document 2: Carbon vol. 43, 2005, p. 1563
non-patent document 3: Carbon vol. 37, 1999, p. 2049

DISCLOSURE OF THE INVENTION

Problems to be Solved by the Invention

However, the method of patent document 1 shows induction of a tissue such as a bone tissue (new bone) only in material surface layer part in clinical practice, since the communication part consisting of linked spherical opened pores has a small pore size and is free of orientation. In the method of patent document 2, the material shrinks during firing. Therefore, an implant material with a desired size cannot be obtained without re-forming after firing. As a result, the step becomes complicated and the method has low practicality since it includes connecting many beads with a nylon wire and the like.

The present inventors have performed a reproducing test of the methods described in patent documents 3 and 4, and found that a nonuniform phase is formed due to the supercooling phenomenon of the slurry in the vicinity of the cooled surface, and pore formation increases as the distance from the cooled surface increases, thus resulting in nonuniform pore shape between the upper and lower sides (see Comparative Example 3 of the present specification). For these reasons, it has been clarified that the methods have a problem in that they cannot produce an implant material with a sufficiently long oriented continuous pore. Consequently, it has been found that patent documents 3 and 4 cannot provide a specific or practical guidance for a material which allows quick permeation of tissue fluids and body fluids such as blood, bone marrow fluid and the like, through the inside of the material.

In addition, non-patent documents 1-3 and patent document 5 relate to production methods of porous body, including sol-gel transition by a condensation reaction of silica, titania and the like and an acetalization reaction of retinol and formaldehyde. When a porous calcium phosphate-based material is used as an artificial bone, a production method having a risk of causing a new chemical reaction accompanying denaturation and heterogeneity of raw materials and additives is not desirable for use for an artificial bone and the like designed to be implanted in the living body, from the aspects of ensured safety for the living body.

The present invention has been made in view of the above-mentioned situation, and aims to provide an efficient method of producing a porous ceramics material, which rapidly leads formation of a tissue, for example, bone tissue, without using a material that causes a new chemical reaction during the production step and has a practical strength, and a unidirectionally oriented and penetrating pore.

Means of Solving the Problems

To solve the above-mentioned problems, the present inventors have completed the present invention having the following characteristics.

Accordingly, the present invention relates to the following.
(1) A method of producing a porous ceramics material, comprising
step (A): a step of preparing a slurry by dispersing a ceramics raw material in a medium,
step (B): a step of filling the slurry in a container, and inserting the container in a given direction into a cooling medium having a temperature not higher than the freezing point of the slurry such that the slurry freezes unidirectionally from one end side,
step (C): a step of drying the frozen slurry to give a green body, and
step (D): a step of firing the green body.

(2) The production method of the above-mentioned (1), wherein the ceramics is calcium phosphate-based ceramics.
(3) The production method of the above-mentioned (2), wherein the ceramics raw material is hydroxyapatite and/or tricalcium phosphate.
(4) The production method of any of the above-mentioned (1) to (3), wherein a condensation type polymer is added to the slurry in the step (A).
(5) The production method of any of the above-mentioned (1) to (4), wherein the immersion speed of the container is controlled in step (B) such that the crystal growth speed due to freezing of the medium in the slurry and the immersion speed of the container into the cooling medium are almost the same.
(6) The production method of any of the above-mentioned (1)-(5), wherein the medium in the slurry is water, and the immersion speed of the container into the cooling medium in step (B) is 1-200 mm/h.
(7) The production method of any of the above-mentioned (1) to (6), wherein the content of the ceramics raw material in the slurry is 10-60 wt % of the total weight of the slurry.
(8) A method of producing a ceramics raw material-containing slurry frozen body, comprising
step (A): a step of preparing a slurry by dispersing a ceramics raw material in a medium, and
step (B): a step of filling the slurry in a container, and inserting the container in a given direction into a cooling medium having a temperature not higher than the freezing point of the slurry such that the slurry freezes unidirectionally from one end side,
wherein the immersion speed of the container is controlled in step (B) such that the crystal growth speed due to freezing of the medium in the slurry and the immersion speed of the container into the cooling medium are almost the same.
(9) The production method of the above-mentioned (8), wherein the ceramics is calcium phosphate-based ceramics.
(10) The production method of the above-mentioned (8) or (9), wherein the medium in the slurry is water, and the immersion speed of the container into the cooling medium in step (B) is 1-200 mm/h.
(11) The production method of any of the above-mentioned (8) to (10), wherein the content of the ceramics raw material in the slurry is 10-60 wt % of the total weight of the slurry.
(12) A porous ceramics material produced by the method of any of the above-mentioned (1) to (7).

Effect of the Invention

The present invention produces a porous ceramics material, which allows tissue fluid and body fluid such as blood or bone marrow fluid and the like to smoothly permeate through its inside, has a high compressive strength in the direction thereof and a bending strength in the direction perpendicular thereto, and is particularly suitable for artificial bone and the like, especially, a porous calcium phosphate-based ceramics material, conveniently and efficiently.

In addition, a ceramics raw material-containing slurry frozen body that can afford the above-mentioned porous ceramics material by merely drying and firing can be easily and efficiently produced.

| Explanation of Symbols | |
|---|---|
| 11 | porous ceramics material |
| 12 | pore |
| 21 | slurry |
| 31 | container |
| 41 | cooling medium |
| 51 | particles of ceramics raw material |
| 61 | crystal of medium |
| 62 | pore |
| 70 | power source |
| 71 | freezing apparatus |

BEST MODE FOR CARRYING OUT THE INVENTION

The present invention is explained in the following by referring to its preferable embodiment.

First, the porous ceramics material produced by the present invention is explained. In the following description, the porous ceramics material produced by the present invention is also simply indicated as "the porous ceramics material of the present invention", "the material obtained by the present invention" or "the material of the present invention".

The porous ceramics material of the present invention is preferably a porous calcium phosphate-based ceramics material. The porosity of the porous ceramics material of the present invention is preferably 40-90%, more preferably 50-90%, further preferably 60-90%. When the porosity is not less than 40%, sufficient formation of a tissue, for example, bone tissue is expected, since much tissue fluid and body fluid such as blood, bone marrow fluid and the like permeate into the material. When the porosity is not more than 90%, the porous ceramics material is highly strong.

The porosity is measured in conformity to JIS R 1634. Specifically, the following is performed. A diameter 6 mm×height 8 mm cylindrical test piece is cut out from an evaluation target porous ceramics material. The weight and volume of the test piece are measured and the porosity is calculated according to the following formulas.

bulk density=(weight of test piece)/(volume of test piece)

porosity=(1−bulk density/theoretical density)×100

Figure 1:
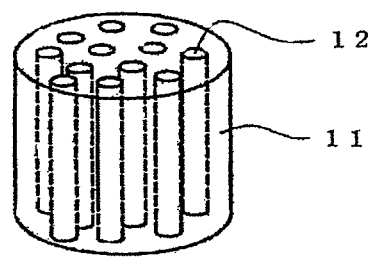
FIG. 1 is a schematic diagram of the porous ceramics material prepared in the present invention.

FIG. 1 is a schematic diagram of the porous ceramics material of the present invention. In the material of the present invention, pores 12 are unidirectionally oriented as shown in FIG. 1. The pore 12 is a region of an empty space without a ceramics substance inside a ceramics material 11. The pores being unidirectionally oriented means that pores extending in the uniaxial direction are present and the major axis direction of such pores is arranged to be substantially unidirectional. More specifically, for example, the major axis direction of not less than half, preferably not less than 80%, of the pores extending in the uniaxial direction in the ceramics material is arranged to fall, for example, within the range of 30°. The "angle" here means an intersection angle of orthogonal projection of the major axis of void on any flat plane.

The cross sectional area perpendicular to the orientation direction of each pore is preferably $0.05 \times 10^{-3}$–$100 \times 10^{-3}$ mm$^2$, more preferably $0.05 \times 10^{-3}$–$50 \times 10^{-3}$ mm$^2$. The above-mentioned range is a sufficient size to be passed through by the tissue fluid and body fluid such as blood, bone marrow fluid and the like, at which the tissue fluid and body fluid such as blood, bone marrow fluid and the like can easily pass by the capillary phenomenon. To solve the problem of the present invention, however, it is not necessary for all pores in the material to have the above-mentioned cross sectional area. In addition, for the cell etc. contained in the tissue fluid and body fluid such as blood, bone marrow fluid and the like to penetrate into a porous ceramics material, a pore in the cross section perpendicular to the orientation direction has a minor axis of at least 10 μm, preferably 20 μm, more preferably not less than 30 μm. On the other hand, the major axis of a pore in the cross section perpendicular to the orientation direction is preferably within the range of at least the same length as the minor axis-500 μm, more preferably 30 μm-300 μm, to ensure the strength.

The length of the pore in the major axis direction is preferably not less than 5 mm, more preferably not less than 10 mm, still more preferably not less than 20 mm, particularly preferably not less than 30 mm. The length does not have a particular upper limit. When the pore has a sufficient length, an implant material and the like can be obtained easily by processing such as cutting etc. To solve the problem of the present invention, however, it is not necessary for all pores in the material to have the above-mentioned length.

In a preferable embodiment, a pore has a cross sectional area perpendicular to the orientation direction of $0.05 \times 10^{-3}$–$100 \times 10^{-3}$ mm$^2$, more preferably $0.05 \times 10^{-3}$–$50 \times 10^{-3}$ mm$^2$, for at least 5 mm length in the orientation direction. In this case, good permeation of the tissue fluid and body fluid such as blood, bone marrow fluid and the like can be achieved for a practically sufficient length. It is not necessary for all pores in the material of the present invention to have the above-mentioned cross sectional area.

From the aspects of the balance between rapid infiltration of a biological tissue of the tissue fluid and body fluid such as blood, bone marrow fluid and the like and strength, in the material of the present invention, the pore volume ratio of the pore size of not less than 30 μm is preferably within the range of 30-99%, more preferably 70-95%. The "pore size" here means the minor axis.

To determine the cross sectional area of a pore, as in the below-mentioned Examples, a porous calcium phosphate-based material to be measured is embedded in a resin, this is sliced perpendicularly to the oriented axial direction and observed with a electron microscope and the like, and opening areas derived from pores to be focused on can be successively measured. At this time, the material to be measured is cut out every 1 mm and the opening areas in each cross section are measured, whereby the shift, along the orientation length direction of the pores, of the cross sectional area of the pores can be evaluated with a precision suitable for the object of the present invention. In addition, the minor axis and the major axis of a pore can be measured, for example, by measuring the aforementioned images observed by an electron microscope. The pore volume ratio can be measured by the method described in the Examples to be mentioned below.

As mentioned above, when the material is cut out every 1 mm along the pore oriented axial direction and the opening area of the pores in the obtained thin section is measured, the ratio of the maximum opening area to the minimum opening area in a 5 mm length (that is, successive 5 thin sections) where the change in the amount of opening area of the pores is the smallest is preferably within 10-fold, more preferably within 5-fold. Thus, as an implant material, the opening area derived from the pores, namely, the cross sectional area of the pores, preferably shows smaller variation along the orientation direction, since permeation of blood, bone marrow fluid and the like into the material due to the capillary phenomenon becomes smooth. Furthermore, when the ratio is within the range mentioned above, a porous sintered body having a superior strength can be provided, since ceramics layers forming the pores (walls between adjacent voids) are arrayed almost in parallel to each other.

In addition, when a first cross-sectional surface perpendicular to the pore oriented axial direction, and a second cross-sectional surface parallel to the first cross-sectional surface and 30 mm distant in the pore orientation direction from the first cross-sectional surface are focused on, the material of the present invention preferably has an average pore opening area of $0.05 \times 10^{-3}$–$100 \times 10^{-3}$ mm$^2$ in both the first cross-sectional surface and the second cross-sectional surface. Furthermore, when the distance between the first cross-sectional surface and the second cross-sectional surface is 35 mm, the average pore opening area in each of the first cross-sectional surface and the second cross-sectional surface is more preferably within the above-mentioned range.

In a further preferable embodiment, an average pore opening area is $1 \times 10^{-3}$–$100 \times 10^{-3}$ mm$^2$ in both the aforementioned first cross-sectional surface and the second cross-sectional surface.

Since an oriented communicating pore having such a sufficient length and showing less variation in the opening area in the oriented axial direction can be formed, an implant material wherein a biological tissue can rapidly permeate into the inside and quickly form a tissue (new bone) can be realized.

Next, the composition and the production method of the porous ceramics material of the present invention are explained.

Figure 2:
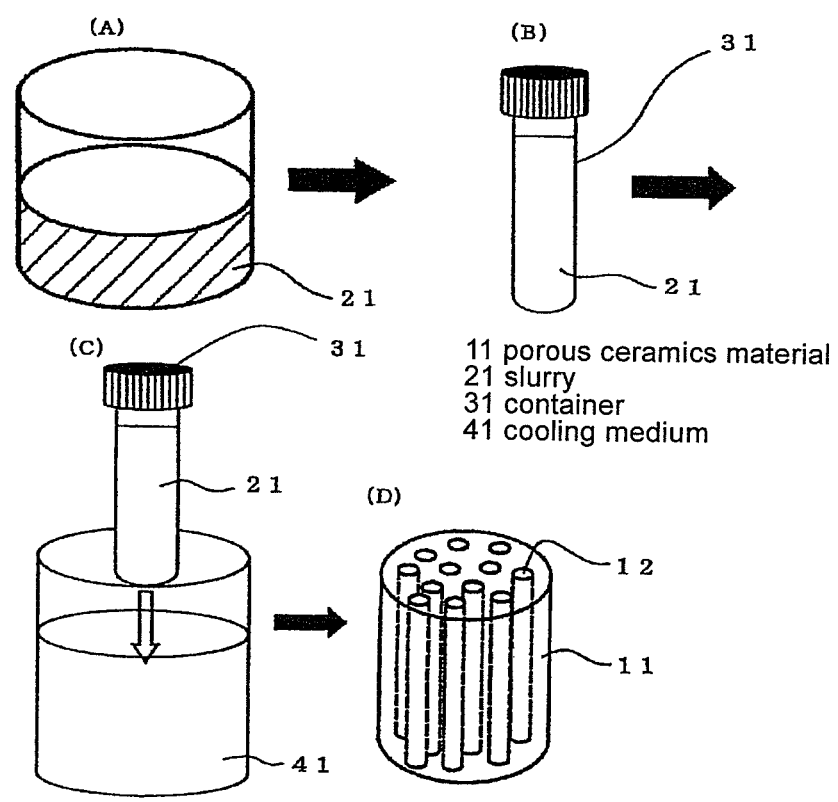
FIG. 2 shows one example of the production method of the present invention.
Figure 3:
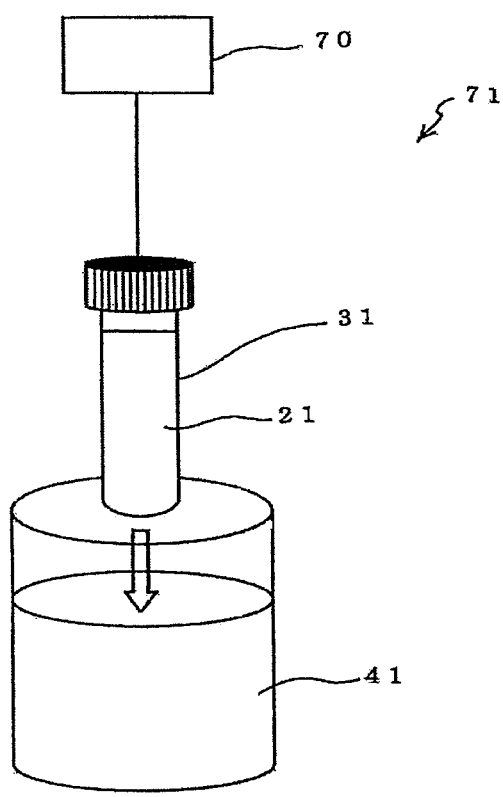
FIG. 3 is a schematic diagram of one example of a freezing apparatus to be used for freezing.

The production method of the porous ceramics material of the present invention includes a step of preparing a slurry including dispersing a ceramics raw material in a medium (step A), a step of filling the obtained slurry in a container, and inserting the container in a cooling medium having a temperature not more than the freezing point of the slurry in a predetermined direction (arrow direction in FIG. 2(*c*) or FIG. 3) to allow the slurry to unidirectionally freeze from one end side (step B), a step of drying the frozen slurry to give a green body (step C), and a step of firing the dried green body (step D).

In step B, a frost column-like crystal of the medium grows since the slurry unidirectionally freezes from one end side. In step C, the crystal of medium is sublimated by drying the frozen slurry, whereby a green body having macropores is obtained. In step D, the green body is fired, whereby a ceramics material having macropores, wherein ceramics particles are densely sintered, can be obtained.

The production method of the present invention is explained in more detail in the following according to each step.

FIG. 2(A) schematically shows preparation of a slurry. Slurry 21 to be used for step A can be prepared by dispersing the ceramics raw material in a medium. Here, the "ceramics raw material" refers to particles used for producing the ceramics material, preferably particles used for producing calcium phosphate-based ceramics materials. In addition, the below-mentioned additives are preferably dissolved or dispersed in slurry 21.

Examples of calcium phosphate-based ceramics raw materials include hydroxyapatite, fluorapatite, chlorapatite, tricalcium phosphate, calcium metaphosphate, tetracalcium phosphate, calcium hydrogen phosphate, calcium hydrogen phosphate dihydrate and the like. A mixture of any of these can also be used. In the material of the present invention, a part of Ca component of the calcium phosphate-based ceramics raw material may be substituted by one or more kinds selected from Sr, Ba, Mg, Fe, Al, Y, La, Na, K, Ag, Pd, Zn, Pb, Cd, H and other rare earths. In addition, a part of ($PO_4$) component may be substituted by one or more kinds selected from $VO_4$, $BO_3$, $SO_4$, $CO_3$, $SiO_4$ and the like. Furthermore, a part of (OH) component may be substituted by one or more kinds selected from F, Cl, $CO_3$, I and Br.

For bone formation, the calcium phosphate-based ceramics raw material is preferably hydroxyapatite, fluorapatite, chlorapatite or tricalcium phosphate, more preferably hydroxyapatite or tricalcium phosphate. The calcium phosphate-based ceramics raw material may be derived from natural mineral, or may be chemically synthesized by various wet processes, dry processes and the like.

The content of the ceramics raw material in a slurry is preferably 10-60 wt %, more preferably 10-40 wt %, more preferably 20-25 wt %, relative to the total weight of the slurry.

As a medium to be used for dispersing a ceramics raw material, a medium having sublimation property that can be removed by the below-mentioned lyophilization is preferable. For example, water, tert-butyl alcohol, benzene and the like can be used, with preference given to water. In addition, water having high degree of purification is preferable, and distilled water, ion-exchanged water, purified water, sterilized purified water, water for injection and the like are preferable.

A ceramics raw material is pulverized and granulated to have appropriate particle size distribution according to a known pulverization granulation method. The average particle size of the granulated powder is preferably within the range of 0.1-40 μm, more preferably 0.5-30 μm. When the average particle size is not less than 0.1 μm, handling becomes easy and workability improves. On the other hand, when the average particle size is not more than 40 μm, the ceramics raw material is well dispersed in slurry 21 to easily afford a stable slurry.

To improve dispersibility of slurry by increasing the viscosity of slurry 21, thereby maintaining the form of a ceramics porous formed body before firing and further controlling the crystal grain growth during sintering, an additive is preferably dissolved or dispersed in slurry 21. The additive is not particularly limited as long as it is a compound or composition capable of achieving the aforementioned object. The additive is preferably a condensation type polymer which is an organic compound that burns during sintering to be consumed. In this case, since a ceramics material obtained after firing does not substantially contain a component derived from the additive, the material is superior in safety for living organism. Examples of such additive include gelatin, collagen, poly(glycolic acid), poly(lactic acid), poly(hydroxybutyrate) and the like. In addition, these additives may be used in a combination of one or more kinds. Where necessary, a component other than the above-mentioned components may be added to slurry 21 within the range the object of the present invention is not inhibited.

When an additive is added to a slurry, the amount of the additive to be added is preferably 0.1-20 wt %, more preferably 3-10 wt %, still more preferably 4-8 wt %, relative to the total weight of the slurry.

Slurry 21 can be prepared according to a known method. Typically, slurry 21 can be prepared by adding a ceramics raw material and an additive as necessary while stirring the medium. Slurry 21 is preferably subjected to a degassing treatment. In this case, air bubbles do not remain in the slurry and, as a result, the formation of undesirable pores (defect) caused by air bubbles can be avoided in a sintered body. For a degassing treatment, a known method can be used and, for example, a degassing method by stirring in vacuum, a degassing method by planetary mixing etc. and the like can be used.

FIG. 2(B) and FIG. 2(C) schematically show a step of freezing a slurry in a container (step B). In step B, the slurry 21 obtained in step A is filled in a container 31, and the container 31 is inserted (immersed) in a cooling medium 41 cooled to the freezing point of slurry 21 or below, whereby slurry 21 in the container is unidirectionally frozen from one end side (i.e., end of the tip of container 31 in the insert direction) to give a formed body of the slurry. AS a result of such freezing, frost column-like solidified crystal of the medium is grown and unidirectionally oriented in the formed body.

FIG. 3 is a schematic diagram of one example of a freezing apparatus to be used for freezing.

In the freezing apparatus 71, a cylindrical-shaped container 31 housing the slurry 21 is connected to a suitable power source 70 such as a constant-speed motor and the like, and the container 31 descends from above a cooling medium 41 cooled to the freezing point of slurry or below towards the cooling medium 41 using the aforementioned power source 70 and is inserted (immersed) in the cooling medium 41.

The speed of insertion of container 31 in cooling medium 41, i.e., the immersion speed of container 31 in cooling medium 41 is preferably controlled so that the speed of crystal growth due to freezing of medium in slurry 21 will be almost the same as the immersion speed, since a porous ceramics material having high strength and continuous pore with appropriate pore size can be obtained. The "speed of crystal growth" here can be determined, for example, by scale marking the side wall of container 31, and calculating the movement speed of the frozen surface of the medium in slurry 21 in a container.

It has also been confirmed by setting a temperature sensor at a plurality of heights in the central area (axis area) and near the side wall of container 31, that the temperature of the slurry is almost the same at the same height of the container in the central area (axis area) and near the side wall in the container. That is, it has been confirmed that freezing of slurry proceeds almost uniformly plain-wise in the container, and the crystal of medium also grows plain-wise.

Generally, when water is used as the medium in slurry 21, the immersion speed of container 31 is preferably 1-200 mm/h, more preferably 5-100 mm/h, most preferably 10-50 mm/h. When the immersion speed of container 31 and the speed of crystal growth due to freezing of the medium in slurry 21 are markedly different, for example, when the immersion speed is markedly higher than the speed of crystal growth, freezing of slurry 21 irregularly proceeds from the side surface, upper surface and the like, and an unidirectional frozen body of the medium cannot be achieved. On the other hand, when the immersion speed is markedly smaller than the speed of crystal growth, fusion of medium crystal increasingly occurs toward the upper part of container 31 (i.e., the end on the opposite side from the end of container 31 on the insert direction tip side), thus unpreferably producing a non-uniform frozen body with an increased pore size. In the present invention, the "the immersion speed of container being almost the same as speed of crystal growth due to freezing of medium in slurry" is means that one of the speeds is generally within the range of 50-150%, preferably 80-120%, of the other speed.

In the freezing apparatus 71, slurry is frozen unidirectionally toward the upper direction from the part where the container 31 is dipped in the cooling medium 41 (i.e., direction from the end of the container 31 on the side of the tip of the insert direction into the cooling medium 41 to the other end side of the container 31). The temperature of the cooling medium needs to be lower than the freezing point of the slurry. The temperature of the cooling medium 41 is preferably in the range of the melting point of the medium used for the slurry to 100° C. lower therefrom (i.e., melting point to (melting point −100° C.)), more preferably 15 to 50° C. lower than the melting point of the medium (i.e., (melting point −15° C.) to (melting point −50° C.)). For example, when water is used as the medium, 0° C. to −100° C. is preferable, and −15° C. to −50° C. is more preferable. The growth speed of the crystal depends on the temperature of the cooling medium, where a lower temperature of the cooling medium 41 results in a higher growth speed of the crystal, which permits an increase in the immersion speed. Thus, when crystal with an equivalent shape of a medium is to be formed, the productivity can be improved. The freezing point of the slurry can be easily measured using a differential scanning calorimetry (DSC).

By unidirectionally freezing a slurry in this manner (particularly, by controlling the immersion speed of a container such that the speed of the crystal growth due to freezing of medium in a slurry and the immersion speed of the container will be the same), the medium contained in the slurry becomes long unidirectionally oriented columnar solidified medium component (frost column-like solidified medium component), whereby a ceramics sintered body having pores unidirectionally extending long with a small change in the longitudinal direction in the cross sectional area can be obtained.

The cooling medium 41 is not particularly limited as long as it can cool a slurry to a temperature not more than the freezing point, and liquid helium, liquid nitrogen, liquid oxygen, alcohols such as methanol, ethanol and the like, ketones such as acetone and the like, hydrocarbons such as hexane and the like, ionic liquid and the like can be used. When vaporization, temperature increase and the like of cooling medium due to heat exchange occur, addition of cooling medium or cooling is preferably performed as appropriate to control the liquid surface level and temperature of the cooling medium. To minimize such variations, a sufficient amount of a cooling medium is preferably used for the slurry to be immersed.

The side wall of container 31 is desirably formed from a material having a higher specific heat than that of the medium in which a slurry is dispersed, such as a heat insulating material of polyethylene, polypropylene, vinyl chloride resin, silicone resin, fluororesin and styrene resin, so that the slurry will not freeze, due to the atmosphere above the cooling medium, which is cooled by the cooling medium, from the side wall of the container 31, which is not immersed in the cooling medium. The thickness of the side wall of the container is preferably not less than 0.5 mm. With this thickness, the contained slurry does not easily freeze from the side in contact with the side wall, and the unidirectionally arrayed structure of frost column-like solidified medium component becomes more uniform as designed. The material of the bottom and the side wall of the container 31 may be the same or different. When a different material is used, the bottom of the container 31 is preferably made of a material having a smaller specific heat than that of the medium in which a slurry is dispersed and high thermal conductivity, such as a metal (e.g., iron, copper, brass, stainless steel etc.) and the like.

While the shape of the container is not particularly limited, a cylindrically-shaped container as shown in FIGS. 2, 3 is preferably used since more uniform thermal conductance can be achieved. As explained above, it is important in the present invention that the freezing of slurry proceed almost uniformly plain-wise in a container to allow plain-wise growth of a crystal of medium. When the diameter (inner diameter) of the container is too large, the degree of cooling of the slurry may vary between the central area (axis area) and the vicinity of the side wall of the container to possibly prevent almost uniformly plain-wise progress of freezing. Therefore, when the container is cylindrically shaped, its inner diameter is preferably not more than 200 mm. While the lower limit of the inner diameter of the container is not particularly limited, it is preferably not less than 1 mm so as to afford a green body having pores substantially with a pore size of several dozen to several hundred μm.

In the above-mentioned freezing apparatus 71 (FIG. 3), container 31 filled with slurry 21 is moved and inserted (immersed) in cooling medium 41. In the present invention, however, a constitution wherein a container filled with a slurry is fixed and a cooling medium (cooling medium-containing container) is moved to allow insertion (immersion) of the container filled with the slurry in the cooling medium, or both a container filled with a slurry and a cooling medium (cooling medium-containing container) are moved to insert (immerse) the container filled with the slurry in the cooling medium may be employed.

Figure 4:
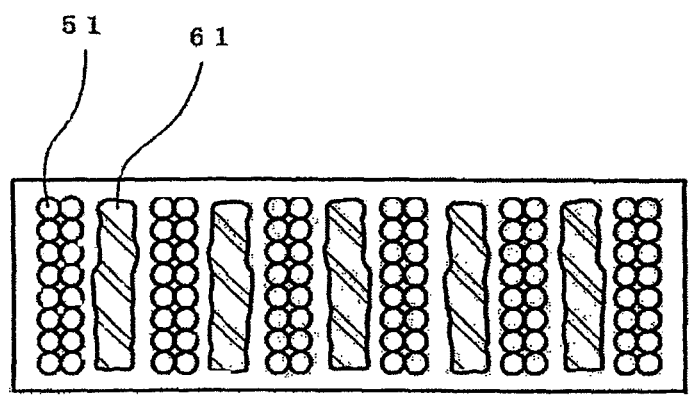
FIG. 4 shows a schematic sectional view of frozen slurry (FIG. 4(A)) and a schematic sectional view of a green body after drying (FIG. 4(B)).
Figure 4:
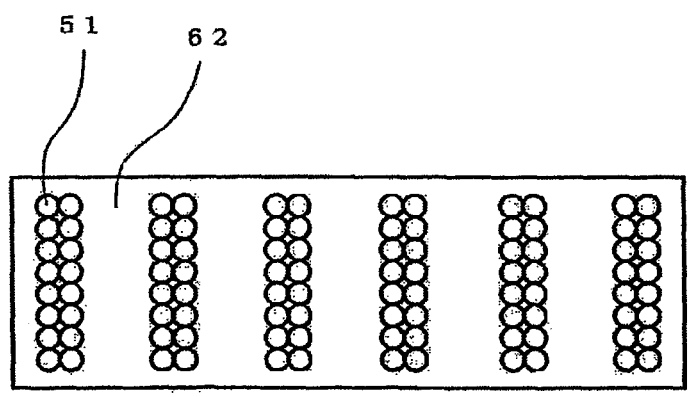

In step C, a green body is obtained by drying a frozen slurry. Typically, a container housing the slurry is lyophilized under reduced pressure as it is. By this operation, a frost column-like solidified medium component is sublimated, and the portion where the solidified medium component was present becomes a pore as a trace of sublimation. Consequently, unidirectionally oriented pores can be formed in the green body. FIG. 4 is a schematic sectional view of a frozen slurry (FIG. 4A) and a green body after drying (FIG. 4B). The frozen slurry contains particles 51, which are ceramics raw material, and substantially unidirectionally arrayed solidified medium component 61. After drying, pores 62 are formed in the region where the solidified medium component 61 was present.

In step D, the obtained green body is fired (FIG. 2D). Typically, the green body obtained in step C is extracted from the container 31, subjected to a suitable shape forming as necessary, and fired at a temperature and sintering time suitable for each ceramics. For sintering (firing), sintering conditions that impart the obtained sintered body with suitable mechanical strength for implantation into the living body, namely, the strength that enables processing at the actual clinical practice, and prevents breakage and the like after implantation into the living body, are desirably employed.

Such sintering conditions can be appropriately determined in consideration of the kind of ceramics, porosity of the porous body, average pore size, orientation of pores and the like. While the energy source to be used for firing is not particularly limited, heat, microwave and the like are generally used. While the firing temperature varies depending on the kind of the ceramics raw material, it is generally preferably 1000-1800° C., more preferably 1200-1600° C. When the firing temperature is less than 1000° C., densification by sintering does not proceed sufficiently, and the strength tends to be low. When it exceeds 1800° C., the sintered body tends to have different crystal state due to melting or phase transition. The firing time is generally about 1-4 hr.

In this way, a porous ceramics sintered body having pores of the trace of sublimation of frost column-like solidified medium component can be prepared. The pores take the form of the aforementioned trace of sublimation, and become continuous pores preferably unidirectionally penetrating the sintered body.

When the porous ceramics sintered body (preferably porous calcium phosphate-based ceramics sintered body) of the present invention is used as a porous ceramics material such as artificial bone, it is preferably formed to have a desired shape and sterilized.

A method of forming into a block is not particularly limited, and a known method can be used. Specific examples include a forming process by mechanical processing, a dry forming process, a wet forming process and the like. Since ceramics materials are generally hard and brittle, the conventional porous ceramics materials having uneven thickness of the ceramics layer showed extremely low machinability. As mentioned above, since the pores are unidirectionally oriented in the ceramics material of the present invention, and the pore size thereof is almost uniform, the thickness of the ceramics layer between penetrating pores is also almost uniform. Hence, the material shows superior machinability as compared to conventional porous ceramics materials.

In addition, the method for forming granules is not particularly limited, and a known method can be used. Specific examples include mechanical pulverization with a molder grinder, a ball mill, a jaw crusher, a hammer crusher and the like, pulverization in a mortar etc., and the like. In addition, the particle size of the pulverized porous ceramics material may be adjusted to be the same with a sieve and the like.

A method of sterilizing the material is not particularly limited, and a known method can be used. Specific examples include high-pressure vapor sterilization method (autoclave), gamma radiation sterilization, EOG sterilization, electron beam sterilization and the like. Of these, the high-pressure vapor sterilization method is widely used as a most common sterilization method.

A porous ceramics material obtained in this way (preferably porous calcium phosphate-based ceramics material) is useful as an implant material to be implanted in the living body such as medical or dental and the like such as artificial bone, artificial dental root and the like, a scaffold for cell culture to be used for regenerative medicine and the like, a drug carrier for drug delivery system (DDS) and the like.

Furthermore, in an attempt to induce tissue, for example, a bone tissue at a higher level, a substance having an action to promote growth of tissue, for example, a bone tissue such as a transforming growth factor (TGF-β1), osteoinductive factor (BMP-2), bone morphogenetic factor (OP-1) and the like may be impregnated in, adsorbed onto or immobilized onto the porous ceramics material of the present invention.

EXAMPLES

The present invention is explained in more detail in the following by referring to Examples, which are not to be construed as limitative.

[Measurement Method of Speed of Crystal Growth Due to Freezing of Medium in Slurry]

The movement speed of a frozen surface of a medium in a slurry was calculated from the scale marks on a container filled with the slurry, based on which the speed of the crystal growth due to freezing of the medium in the slurry was determined. Simultaneously, by setting a temperature sensor at a plurality of heights in the central area (axis area) and near the side wall of the container filled with the slurry, it was confirmed that each temperature was almost the same.

[Measurement Method of Porosity]

The porosity was measured according to JIS R 1634. The detail is as shown below. A cylindrically-shaped test piece (diameter 6 mm×height 8 mm) was cut out from an evaluation target porous ceramics material. The weight and volume of the test piece were measured and the porosity was calculated from the following formula.

bulk density=(weight of test piece)/(volume of test piece)

porosity=(1−bulk density/theoretical density)×100

[Measurement Method of Opening Area]

A measurement target porous calcium phosphate-based ceramics material was embedded in a resin, sliced in the direction perpendicular to the oriented axial direction, and 70-fold enlarged images thereof were observed by scanning electron microscope (SEM), and the opening areas derived from the pores were sequentially measured. As an average value, an average opening area of pores present in a 0.7 mm square was determined.

[Measurement Method of Compressive Strength]

Performed according to JIS R 1608. As the test piece, a cylindrically-shaped test piece (diameter 6 mm×height 8 mm) was used.

[Measurement Method of Pore Length]

To determined the pore length, a measurement target ceramics material was embedded in a resin, sliced in the direction parallel to the oriented axial direction, and 20-fold enlarged images thereof were observed by a scanning electron microscope, based on which the pore length was sequentially measured.

[Measurement Method of Pore Volume Ratio]

The pore size distribution was measured by mercury porosimetry (measurement range: $4\times10^{-3}$–$4\times10^2$ μm). As the test piece, cylindrically-shaped test piece (diameter 6 mm×height 8 mm) was used. The pore volume ratio was calculated from the pore size distribution obtained by mercury porosimetry, and shows the proportion of a pore volume of not less than 30 μm in the total pore volume within the measurement range. The contact angle of mercury and hydroxyapatite was 130°, and the surface tension was 485 mN/m.

Examples 1-5

Figure 8:
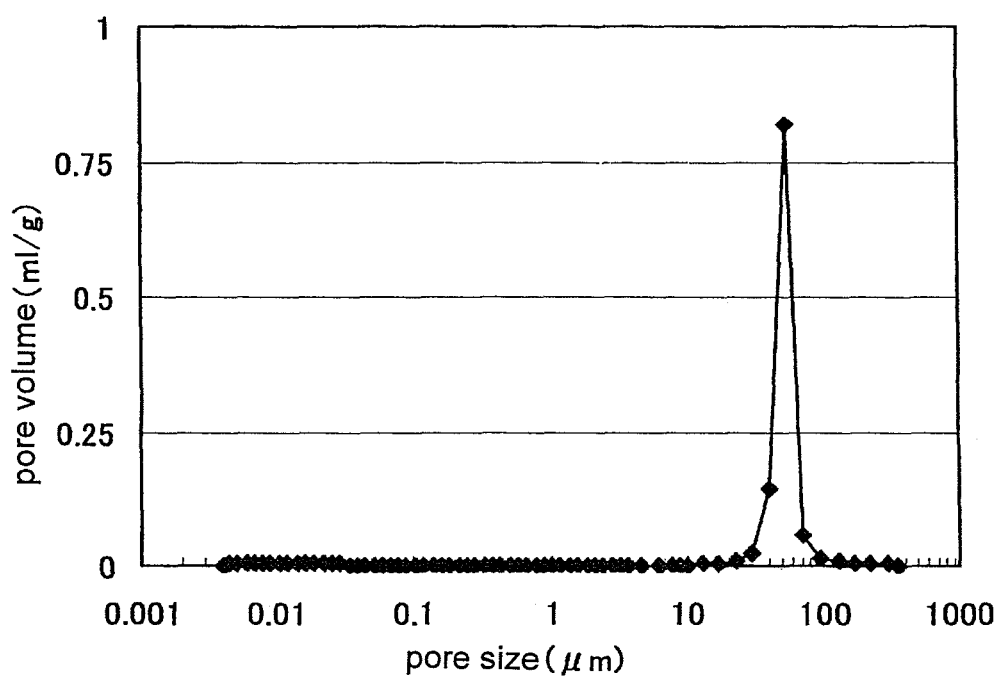
FIG. 8 is a view showing the pore size distribution of the material of Example 2.

A calcium phosphate-based raw material and an additive were dispersed and dissolved in distilled water at the composition shown in Table 1 to give slurry 21. 10 g of slurry 21 was filled in a 15 ml centrifuge tube (made of polypropylene resin) container 31 having an inner diameter of about 16 mm (manufactured by Greiner GmbH (Germany)), and cooled for 3 hr in a refrigerator maintained at 4° C. The container 31 was immersed in an ethyl alcohol bath cooled to −20° C. at a rate shown in Table 1 to form frost column-like ice in the slurry. The thus-obtained frozen body was lyophilized in vacuo, and the dried body was sintered at 1200° C. for 1 hr to give a ceramics material having oriented pores. The ceramics material produced in Example 2 was measured for the pore size distribution according to the mercury porosimetry. The test method followed JIS R 1655:2003. FIG. 8 shows the experimental results obtained in this test. From FIG. 8, it can be confirmed that the ceramics material of the present invention shows pore size distribution with a single peak near pore size 50 μm and no peak at pore size of not more than 0.1 μm, and that ceramics particles had been densely sintered.

Example 6

According to the method of Example 1 except that the temperature of ethyl alcohol bath was set to −40° C., the Example was performed under respective conditions described in Table 1.

Examples 7-10

According to the method of Example 1 except that a 50 ml centrifuge tube (made of polypropylene resin) container 31 having an inner diameter of about 25 mm (manufactured by Greiner GmbH (Germany)) was used and 36 g of a slurry was filled in the container 31, the Example was performed under respective conditions described in Table 1.

Examples 11-16

According to the method of Example 1 except that a dried body was sintered at 1100° C., the Example was performed under respective conditions described in Table 1.

Comparative Examples 1 and 2

A calcium phosphate-based raw material and an additive were dispersed and dissolved in distilled water at the composition shown in Table 1 to give slurry 21. 10 g of slurry 21 was filled in a 15 ml centrifuge tube (made of polypropylene resin) container 31 having an inner diameter of 16 mm (manufactured by Greiner GmbH (Germany)), and cooled for 3 hr in a refrigerator maintained at 4° C. The container 31 was rapidly cooled and frozen in a freezer at −80° C. The thus-obtained frozen body was lyophilized in vacuo, and the dried body was sintered at 1200° C. for 1 hr to give a ceramics material.

Comparative Example 3

Hydroxyapatite and gelatin (additive) were dispersed and dissolved in distilled water at the composition shown in Table 1 to give slurry 21. 4 g of slurry 21 was filled in a pipe-shaped container (diameter 16 mm, height 20 mm) made of a vinyl chloride resin. The container 31 was set on a brass disc cooling plate cooled with liquid nitrogen, and cooled and frozen only from the underside, whereby frost column-like ice was formed in the slurry. The thus-obtained frozen body was lyophilized in vacuo, and the dried body was sintered at 1200° C. for 1 hr to give a highly strong ceramics material having oriented pores.

The production conditions and evaluation results of the ceramics materials of respective Examples and Comparative Examples are shown in Tables 1-3. In Table 2, the first cross-sectional surface (lower side) and the second cross-sectional surface (upper side) were both perpendicular to the orientation direction of the pores and the distance between the both cross-sectional surfaces was 35 mm.

TABLE 1

| item unit | calcium phosphate | slurry composition content wt % | additive | content wt % | medium | content wt % | immersion speed mm/h |
|---|---|---|---|---|---|---|---|
| Example 1 | HAp | 21.8 | gelatin | 4.8 | distilled water | 73.4 | 20 |
| Example 2 | HAp | 21.8 | gelatin | 4.8 | distilled water | 73.4 | 30 |
| Example 3 | HAp | 21.8 | gelatin | 4.8 | distilled water | 73.4 | 15 |
| Example 4 | HAp | 21.8 | gelatin | 4.8 | distilled water | 73.4 | 10 |
| Example 5 | HAp | 21.8 | gelatin | 5.5 | distilled water | 72.7 | 20 |
| Example 6 | HAp | 21.8 | gelatin | 4.8 | distilled water | 73.4 | 25 |
| Example 7 | HAp | 21.8 | gelatin | 4.8 | distilled water | 73.4 | 20 |
| Example 8 | HAp | 21.8 | gelatin | 4.8 | distilled water | 73.4 | 15 |
| Example 9 | HAp | 22.2 | gelatin | 4.7 | distilled water | 73.1 | 20 |
| Example 10 | HAp | 22.2 | gelatin | 4.7 | distilled water | 73.1 | 15 |
| Example 11 | β-TCP | 21.8 | gelatin | 4.8 | distilled water | 73.4 | 20 |
| Example 12 | β-TCP | 21.8 | gelatin | 4.8 | distilled water | 73.4 | 25 |
| Example 13 | β-TCP | 24.5 | gelatin | 4.5 | distilled water | 70.7 | 20 |
| Example 14 | β-TCP | 21.8 | gelatin | 4.8 | distilled water | 73.4 | 12 |
| Example 15 | β-TCP | 21.8 | gelatin | 5.5 | distilled water | 72.7 | 20 |
| Example 16 | β-TCP | 25.0 | gelatin | 4.5 | distilled water | 70.5 | 30 |
| Comparative Example 1 | HAp | 21.8 | gelatin | 4.8 | distilled water | 73.4 | — |
| Comparative Example 2 | β-TCP | 21.8 | gelatin | 4.8 | distilled water | 73.4 | — |
| Comparative Example 3 | HAp | 21.8 | gelatin | 4.8 | distilled water | 73.4 | — |

In Table 1, HAp means hydroxyapatite, and β-TCP means β-tricalcium phosphate.

TABLE 2

| | property of fired body | | | |
|---|---|---|---|---|
| | | | average opening area of pore | |
| item unit | porosity % | pore length mm | first cross-sectional surface ×10$^{-3}$ mm$^2$ | second cross-sectional surface ×10$^{-3}$ mm$^2$ |
| Ex. 1 | 76.8 | >35 | 3.9 | 4.1 |
| Ex. 2 | 76.2 | >35 | 2.9 | 3 |
| Ex. 3 | 76.8 | >35 | 10 | 10.5 |
| Ex. 4 | 76.9 | >35 | 31.3 | 40.5 |
| Ex. 5 | 78.7 | >35 | 4 | 4 |

TABLE 2-continued

| | | | property of fired body | |
| | | | | average opening area of pore |
| item unit | porosity % | pore length mm | first cross-sectional surface ×10⁻³ mm² | second cross-sectional surface ×10⁻³ mm² |
| --- | --- | --- | --- | --- |
| Ex. 6 | 77.7 | >35 | 5 | 5.4 |
| Ex. 7 | 78.1 | >35 | 3.7 | 3.9 |
| Ex. 8 | 77.1 | >35 | 5.9 | 6.2 |
| Ex. 9 | 76.2 | >35 | 3.8 | 4 |
| Ex. 10 | 76.2 | >35 | 4.4 | 4.9 |
| Ex. 11 | 76.6 | >35 | 2 | 2.1 |
| Ex. 12 | 76.9 | >35 | 1.3 | 1.4 |
| Ex. 13 | 70.7 | >35 | 2.1 | 2.2 |
| Ex. 14 | 77 | >35 | 3.3 | 3.5 |
| Ex. 15 | 77 | >35 | 2 | 2 |
| Ex. 16 | 65.9 | >35 | 3.1 | 3.1 |
| Comp. Ex. 1 | 77.3 | — | — | — |
| Comp. Ex. 2 | 74.1 | — | — | — |
| Comp. Ex. 3 | 76.6 | 4 | 5.1 | 333 |

TABLE 3

| | property of fired body | |
| item unit | compressive strength MPa | volume ratio of pore with pore size of 30 μm or more (%) |
| --- | --- | --- |
| Example 1 | 15.2 | 89.6 |
| Example 2 | 14.7 | 89.2 |
| Example 3 | 13.2 | 89.3 |
| Example 4 | 5.7 | 90.1 |
| Example 5 | 12.3 | 87.6 |
| Example 6 | 11.1 | 88.7 |
| Example 7 | 11 | 89.9 |
| Example 8 | 6.2 | 88.8 |
| Example 9 | 11.1 | 90.2 |
| Example 10 | 9 | 90.2 |
| Example 11 | 3.9 | 36.2 |
| Example 12 | 3.4 | 42.6 |
| Example 13 | 1.1 | 37.7 |
| Example 14 | 1.6 | 36.9 |
| Example 15 | 4.4 | 39.8 |
| Example 16 | 12.3 | 46.8 |
| Comparative Example 1 | 5.9 | 56.7 |
| Comparative Example 2 | 1.4 | 29.8 |
| Comparative Example 3 | 1.1 | 84.4 |

From the above-mentioned results of Examples 1-16, it is clear that the porous calcium phosphate-based material obtained by the production method of the present invention has properties suitable for use as artificial bone and the like. In Examples 1-4 employing the same slurry composition and using the containers of the same size for cooling, the speed of crystal growth due to freezing of medium in slurry was observed and found to be 20 mm/h. In Example 6 setting the temperature of ethyl alcohol bath to −40° C., the speed of crystal growth due to freezing of medium in slurry was observed and found to be 25 mm/h.

Particularly, it was found that a material having high strength and continuous pores with a suitable pore size was obtained in Examples 1 and 6, wherein the immersion speed was controlled such that the speed of the crystal growth due to freezing of medium in a slurry and the immersion speed were the same, from among the Examples 1-4 and 6.

Figure 5:
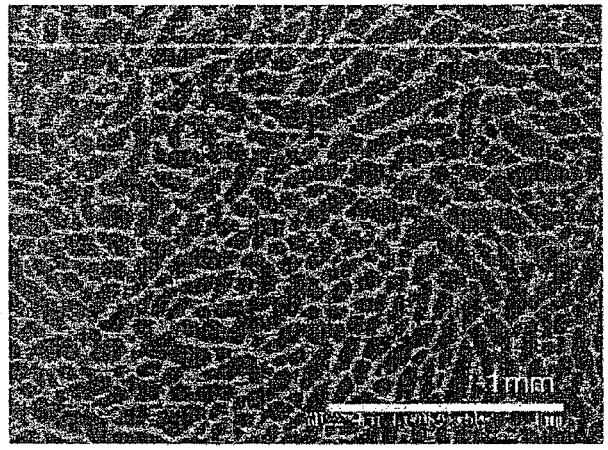
FIG. 5 shows SEM-observed image of the cross section of the material produced in Example 1.
Figure 5:
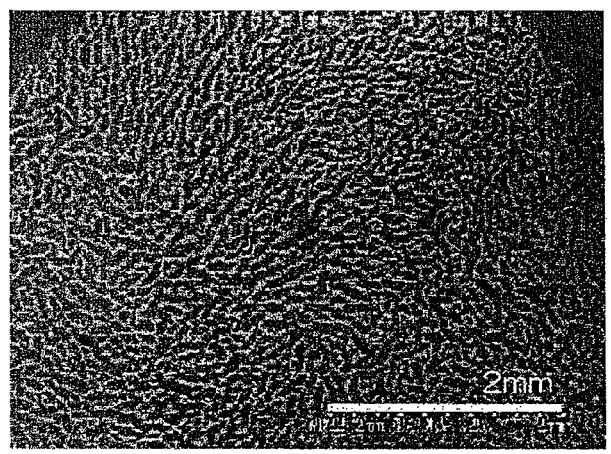
Figure 5:
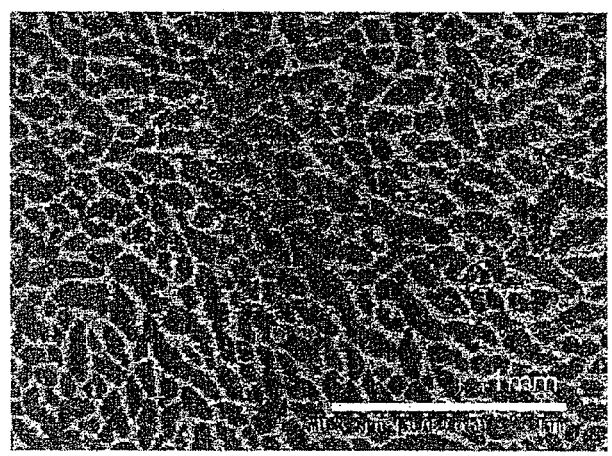

FIG. 5 shows an SEM-observed image of the cross section of a test piece obtained by impregnating the material prepared in Example 1 with epoxy resin.

FIGS. 5(A) and 5(B) show observed images (with different magnifications) of the same cross section perpendicular to the pore orientation direction, and FIG. 5(C) shows an observed image of a cross section parallel to FIGS. 5(A) and 5(B) and 35 mm distant therefrom. The magnification was 50-fold in FIG. 5(A) and FIG. 5(C), and 25-fold in FIG. 5(B).

Figure 6:
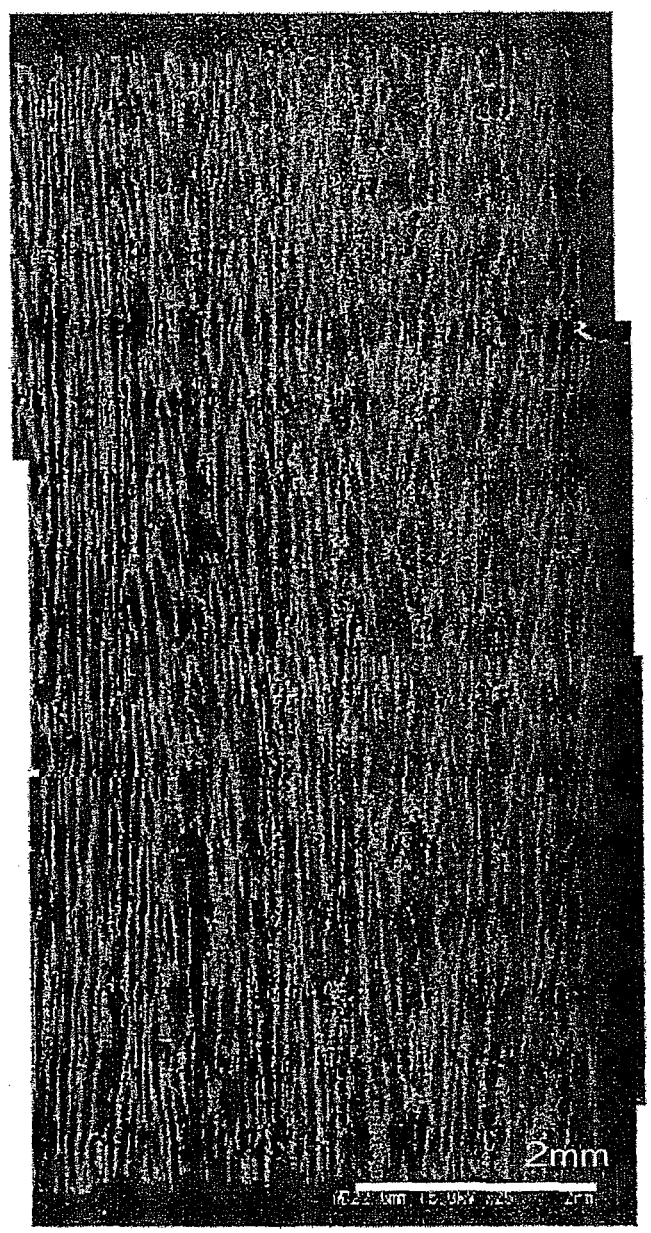
FIG. 6 is an SEM-observed image of a cross section of the material prepared in Example 1.
Figure 7:
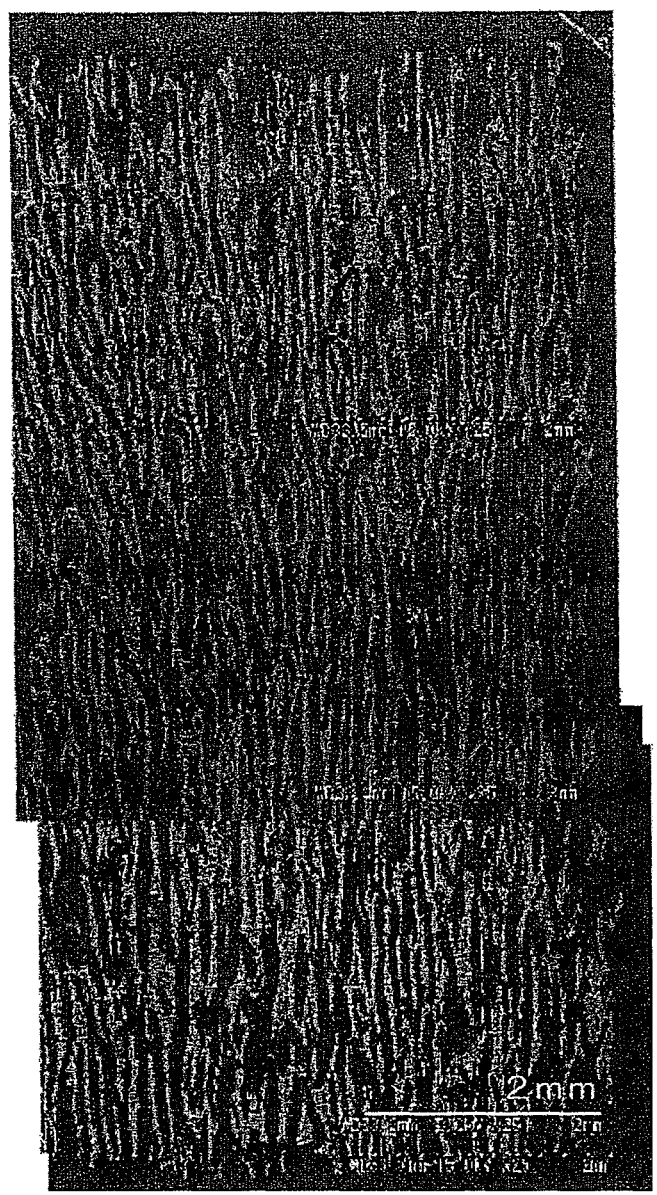
FIG. 7 is an SEM-observed image of a cross section of the material prepared in Example 1.

FIGS. 6 and 7 show an SEM-observed image (magnification: ×25) of the cross section of the material prepared in Example 1, where a plurality of observed images of the cross section parallel to the pore orientation direction are connected.

FIG. 6 shows an observed image of a test piece cut for 8 mm from the upper part and FIG. 7 shows an observed image of a test piece cut for 8 mm from the lower part. In each Figure, pores are present over the length of not less than 35 mm.

Figure 9:
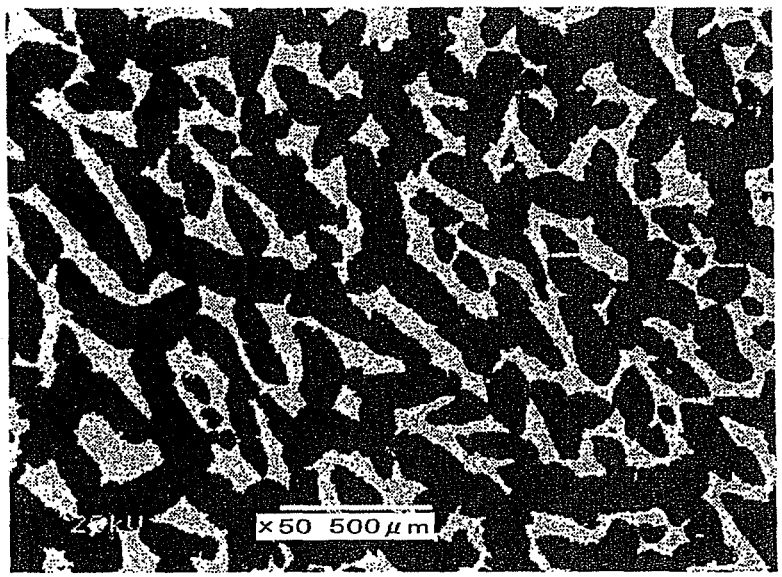
FIG. 9 is SEM-observed image of the cross section of the material prepared in Comparative Example 3.
Figure 9:
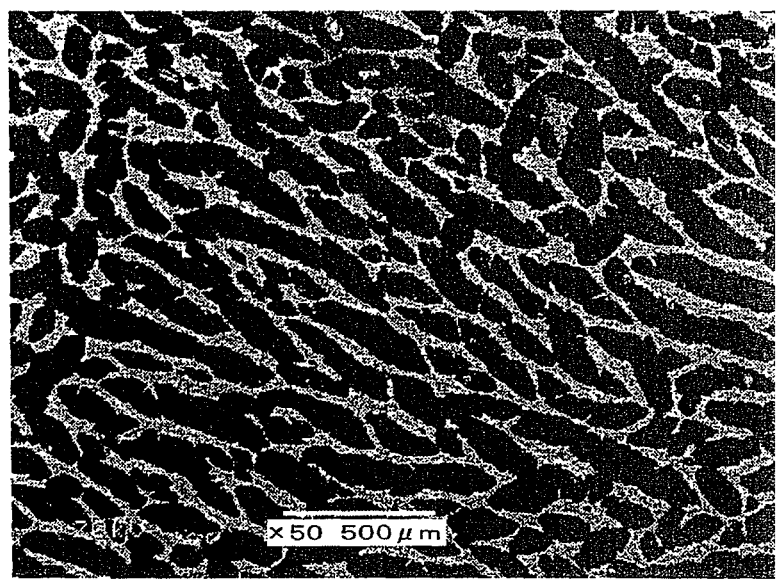

FIG. 9 shows an SEM-observed image (magnification: ×50) of the cross section of the material prepared in Comparative Example 3.

Figure 10:
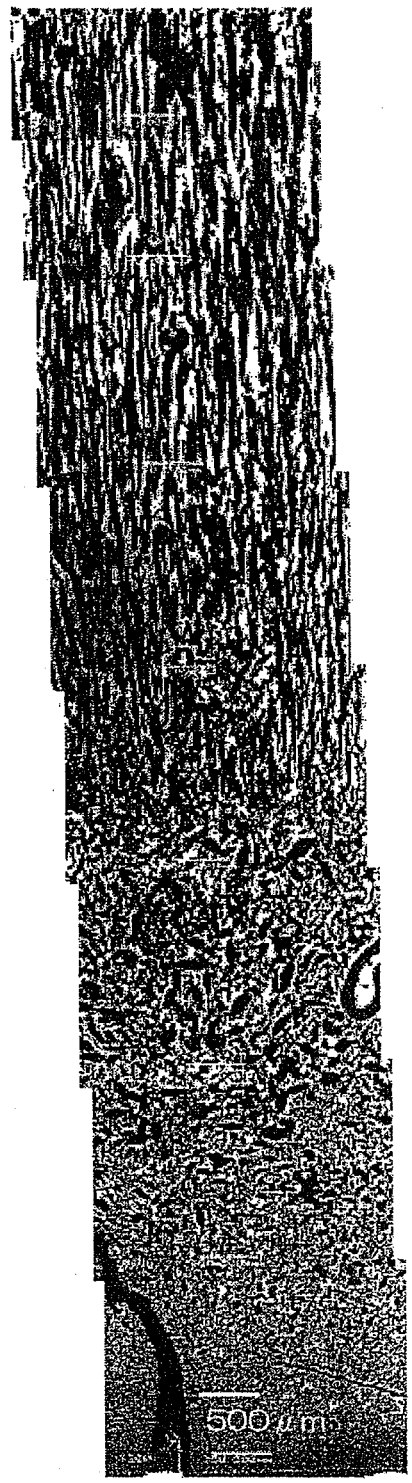
FIG. 10 is an SEM-observed image of a cross section of the material prepared in Comparative Example 3.

FIG. 9(A) shows an observed image of the same cross section perpendicular to the pore orientation direction, and FIG. 9(B) shows an observed image of the cross section parallel to FIG. 9(A) and about 10 mm distant therefrom. By comparison of FIG. 9(A) and FIG. 9(B), it is clear that FIG. 9(A) showing the upper part has greater pores than those of FIG. 9(B) showing the lower part, evidencing different pore sizes between the upper part and the lower part. FIG. 10 shows an SEM-observed image (magnification: ×40) of the cross section of the material prepared in Comparative Example 3, where a plurality of observed images of the cross section parallel to the pore orientation direction are connected. It is also clear from FIG. 10 that the pores expanded more in the upper part (upper part in Figure) as the distance from the cooled surface increased, and a heterogeneous phase considered to result from the supercooling phenomenon was formed in the vicinity of the cooled surface (lower part in Figure).

[Evaluation of Cell Invasion]

The property of the material as a cell culture scaffold was evaluated by examining the cell invasion by the following method.

A test piece, which was prepared in Example 2 and formed into a cylindrical shape (φ6 mm, height 10 mm), was previously immersed in a culture medium to allow impregnation of the porous body with the culture medium. 50 μL of a suspension (5×10⁵ cells) of human osteosarcoma-derived cells (MG63) was seeded on the upper side (φ6 mm) of the test piece, and the cells were cultured at 37° C. 3 days later, the test piece was taken out, the cells were fixed with 2% glutaraldehyde solution, and the test piece was divided in parallel to the orientation direction of the pore, such that the surface seeded with the cells formed a semicircle. The obtained porous body was stained with Giemsa stain solution and observed under an optical microscope.

Figure 11:
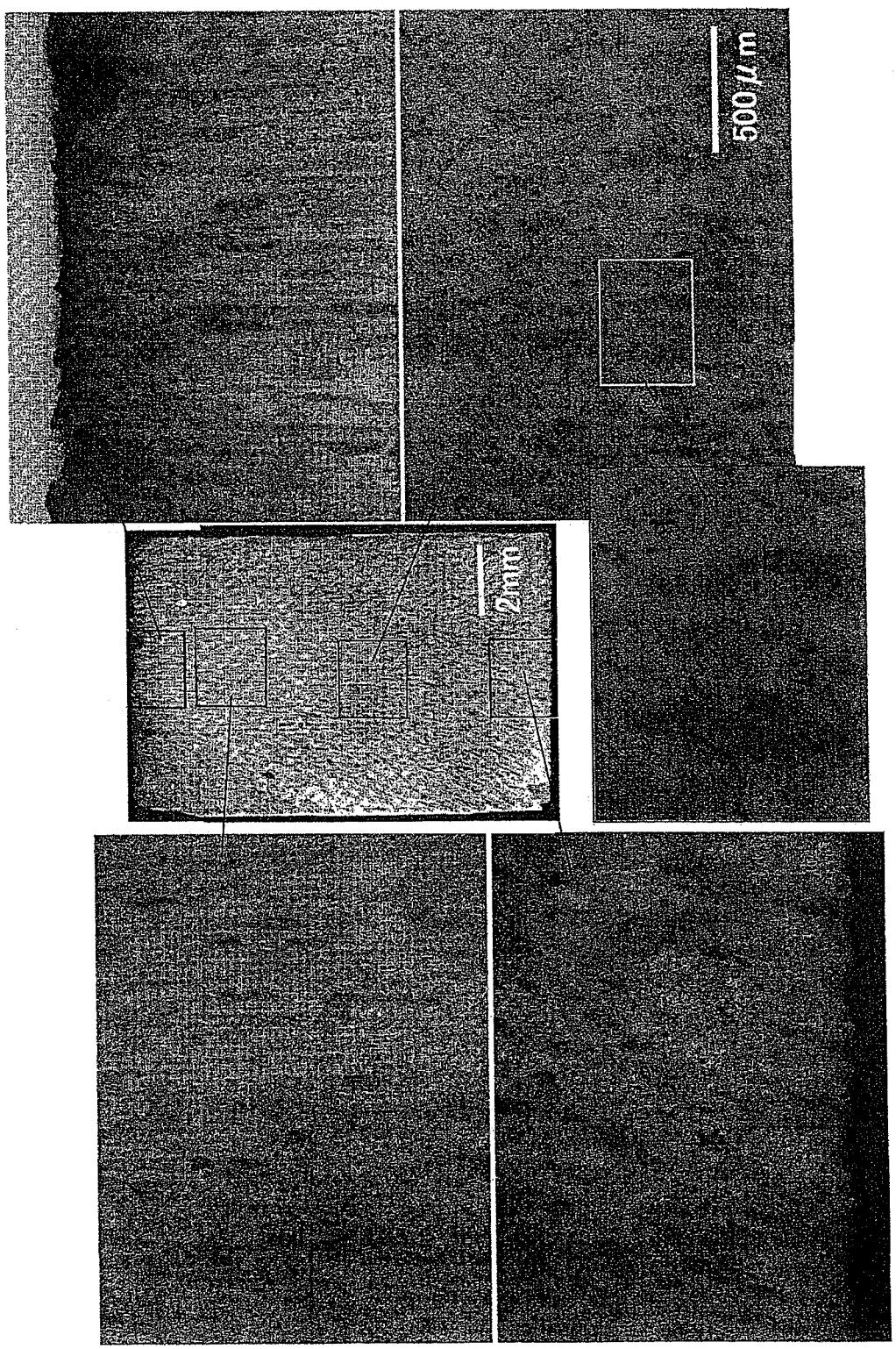
FIG. 11 shows light microscopic images observed, evaluating the cell invasion performance of the material produced in the Example.

FIG. 11 shows the cell invasion evaluation results. The part stained with the Giemsa stain solution showed cell invasion, and the cells invaded from the upper side, where the cells were seeded, to the center and lower part of the test piece. The cells are present in the darkest part in the Figure (dot dispersion).

INDUSTRIAL APPLICABILITY

According to the present invention, the medium contained in the slurry becomes long unidirectionally oriented columnar solidified medium component, whereby a porous ceramics sintered body having pores unidirectionally extending long with a small change in the longitudinal direction in the cross sectional area can be obtained. The porous ceramics sintered body can be used as an implant material to be implanted in the living body such as medical or dental and the like, scaffold for cell culture to be used for regenerative medicine and the like, a drug carrier for drug delivery system (DDS) and the like.

This application is based on a patent application No. 2007-062282 filed in Japan, the contents of which are incorporated in full herein by this reference.

The invention claimed is:

1. A method of producing a porous ceramics material, comprising
    step (A): a step of preparing a slurry by dispersing a ceramics raw material in a medium,
    step (B): a step of filling the slurry in a container, and inserting the container in a given direction and at an insert speed into a cooling medium having a temperature not higher than the freezing point of the slurry such that the slurry freezes unidirectionally at a crystal growth speed from one end side,
    step (C): a step of drying the frozen slurry to give a green body, and
    step (D): a step of firing the green body,
    wherein
    the ceramics is a calcium phosphate-based ceramics,
    the porous ceramics material has unidirectionally penetrating continuous pores and a pore volume ratio of pores having a pore size of not less than 30 relative to total pore volume of 30%-99%,
    the medium in the slurry is water,
    the insert speed of the container is controlled in step (B) such that the crystal growth speed due to freezing of the medium in the slurry and the insert speed of the container into the cooling medium are within the range of 50-150% of each other, and
    the insert speed of the container into the cooling medium in step (B) is 10-50 mm/h.

2. The production method of claim 1, wherein the ceramics raw material is hydroxyapatite and/or tricalcium phosphate.

3. The production method of claim 1, wherein a condensation type polymer is added to the slurry in the step (A).

4. The production method of claim 1, wherein the content of the ceramics raw material in the slurry is 10-60 wt % of the total weight of the slurry.

5. A porous calcium phosphate-based ceramics material having unidirectionally penetrating continuous pores, a first cross-sectional surface perpendicular to the pore oriented axial direction, and a second cross-sectional surface parallel to the first cross-sectional surface,
    wherein a pore volume ratio of pores having a pore size of not less than 30 μm relative to total pore volume is 30%-99%, and
    wherein, when the distance between the first cross-sectional surface and the second cross-sectional surface is 35 mm in the pore orientation direction, the material has an average pore opening area of $0.05\times10^{-3}$ to $100\times10^{-3}$ mm$^2$ in both the first cross-sectional surface and the second cross-sectional surface.

* * * * *

UNITED STATES PATENT AND TRADEMARK OFFICE
CERTIFICATE OF CORRECTION

PATENT NO. : 8,524,128 B2  Page 1 of 1
APPLICATION NO. : 12/531127
DATED : September 3, 2013
INVENTOR(S) : Kuwayama et al.

It is certified that error appears in the above-identified patent and that said Letters Patent is hereby corrected as shown below:

IN THE CLAIMS

Claim 1, column 17, line 30, "30 relative" should read "30 µm relative"

Signed and Sealed this
Eighteenth Day of March, 2014

Michelle K. Lee
*Deputy Director of the United States Patent and Trademark Office*